United States Patent
Pickett et al.

(10) Patent No.: US 11,096,600 B2
(45) Date of Patent: Aug. 24, 2021

(54) DEMODULATING A SIGNAL FROM INTERMITTENTLY ILLUMINATED REGION

(71) Applicant: Intel Corporation, Santa Clara, CA (US)

(72) Inventors: Matthew D. Pickett, San Francisco, CA (US); Jason M. Seitz, San Francisco, CA (US)

(73) Assignee: Intel Corporation, Santa Clara, CA (US)

( * ) Notice: Subject to any disclaimer, the term of this patent is extended or adjusted under 35 U.S.C. 154(b) by 690 days.

(21) Appl. No.: 16/061,509

(22) PCT Filed: Dec. 22, 2015

(86) PCT No.: PCT/US2015/067502
§ 371 (c)(1),
(2) Date: Jun. 12, 2018

(87) PCT Pub. No.: WO2017/111963
PCT Pub. Date: Jun. 29, 2017

(65) Prior Publication Data
US 2020/0260970 A1    Aug. 20, 2020

(51) Int. Cl.
*H05B 45/12* (2020.01)
*H05B 45/32* (2020.01)
(Continued)

(52) U.S. Cl.
CPC ...... *A61B 5/02416* (2013.01); *A61B 5/02438* (2013.01); *A61B 5/7203* (2013.01);
(Continued)

(58) Field of Classification Search
None
See application file for complete search history.

(56) References Cited

U.S. PATENT DOCUMENTS 4,353,152 A   10/1982   O'Connor et al.
5,471,665 A   11/1995   Pace et al.
(Continued)

FOREIGN PATENT DOCUMENTS

CN   1923312     3/2007
CN   101484065   7/2009
(Continued)

OTHER PUBLICATIONS

"Japanese Application Serial No. 2018-525374, Response filed Feb. 12, 2020 to Notification of Reasons for Refusal dated Nov. 12, 2019", w English claims, 15 pgs.
(Continued)

*Primary Examiner* — Dedei K Hammond
(74) *Attorney, Agent, or Firm* — Schwegman Lundberg & Woessner, P.A.

(57) ABSTRACT

A system may intermittently illuminate a region, detect light from the intermittently illuminated region to form a detected signal, and process the detected signal with a demodulator. The demodulator may include a capacitor having an input to receive the detected signal, a resistor having an input connected to an output of the capacitor at a connection point, and a switch that connects the connection point to ground during times when the region is not illuminated. An output of the resistor may produce an output signal that is a high-pass filtered version of the detected signal during times when the region is illuminated, and a time-invariant ground signal during times when the region is not illuminated. Such a demodulator may reduce the effects of low-frequency noise sources, such as background light, op-amp offsets related to input bias, photodiode 1/f noise and dark current.

20 Claims, 7 Drawing Sheets

(51) Int. Cl.
  *A61B 5/024* (2006.01)
  *A61B 5/00* (2006.01)
  *A61B 34/20* (2016.01)
  *G01J 1/44* (2006.01)

(52) U.S. Cl.
  CPC ............ *A61B 5/725* (2013.01); *A61B 5/7228* (2013.01); *A61B 34/20* (2016.02); *G01J 1/44* (2013.01); *H05B 45/12* (2020.01); *H05B 45/32* (2020.01)

(56) References Cited

U.S. PATENT DOCUMENTS

| | | | |
|---|---|---|---|
| 6,891,868 | B2 | 5/2005 | Verboom et al. |
| 7,508,497 | B2 | 3/2009 | LaBelle |
| 7,535,071 | B2 | 5/2009 | Schell et al. |
| 7,988,638 | B2 | 8/2011 | Novac |
| 9,072,439 | B2 | 7/2015 | Kassim et al. |
| 2003/0036685 | A1 | 2/2003 | Goodman |
| 2011/0137181 | A1 | 6/2011 | Lin et al. |
| 2012/0203077 | A1* | 8/2012 | He ................ A61B 5/6815 600/301 |
| 2013/0108280 | A1* | 5/2013 | Azadeh ............ H04B 10/695 398/210 |
| 2013/0296673 | A1 | 11/2013 | Thaveeprungsriporn et al. |
| 2014/0323844 | A1 | 10/2014 | Deliwala et al. |
| 2015/0018649 | A1 | 1/2015 | Lisogurski et al. |
| 2015/0119751 | A1 | 4/2015 | Stanslaski et al. |

FOREIGN PATENT DOCUMENTS

| | | |
|---|---|---|
| CN | 102715893 | 10/2012 |
| CN | 104939812 | 9/2015 |
| CN | 109414169 | 3/2019 |
| DE | 112015007214 | 9/2018 |
| JP | S54155080 | 12/1979 |
| JP | S5879348 | 5/1983 |
| JP | 6359929 | 3/1988 |
| JP | H02151736 | 6/1990 |
| JP | H11132846 | 5/1999 |
| JP | 2006332846 | 12/2006 |
| JP | 2013527721 | 6/2013 |
| JP | 2019502424 | 1/2019 |
| WO | WO-2017111963 A1 | 6/2017 |

OTHER PUBLICATIONS

"Japanese Application Serial No. 2018-525374, Final Notification of Reasons for Refusal dated Jul. 7, 2020", w English translation, 8 pgs.

"International Application Serial No. PCT/US2015/067502, International Search Report dated Sep. 21, 2016", 4 pgs.

"International Application Serial No. PCT/US2015/067502, Written Opinion dated Sep. 21, 2016", 6 pgs.

"Japanese Application Serial No. 2018-525374, Voluntary Amendment filed Jul. 18, 2018", w English claims, 8 pgs.

"Chinese Application Serial No. 201580085218.4, Office Action dated Nov. 14, 2018", W English Translation, 5 pgs.

"Japanese Application Serial No. 2018-525374, Notification of Reasons for Refusal dated Nov. 12, 2019", w English translation, 11 pgs.

"Japanese Application Serial No. 2018-525374, Response filed Oct. 6, 2020 to Final Notification of Reasons for Refusal dated Jul. 7, 2020", w English claims, 10 pgs.

"Chinese Application Serial No. 201580085218.4, Office Action dated Dec. 2, 2020", w Concise Statement of Relevance, 7 pgs.

\* cited by examiner

US 11,096,600 B2

DEMODULATING A SIGNAL FROM INTERMITTENTLY ILLUMINATED REGION

CLAIM OF PRIORITY

This patent application is a U.S. National Stage Application under 35 U.S.C. 371 from International Application No. PCT/US2015/067502, filed Dec. 22, 2015, published as WO 2017/111963, which is incorporated herein by reference.

TECHNICAL FIELD

This document pertains generally, but not by way of limitation, to circuitry for processing signals from optical detectors.

BACKGROUND

Techniques exist to measure heart rate through a subject's skin using optical sensing. For example, in photoplethysmography, light emitting diodes may illuminate a region of the skin surface, and photodiodes may measure minute changes in the light reflected from blood vessels under the skin surface in order to derive a pulsatile signal that is in synchrony with a heartbeat.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

A system, such as a wearable heart rate monitor, may illuminate a region, such as on a wearer's skin, detect light from the illuminated region to form a detected signal, and extract a measurement, such as a heart rate, from the detected signal. Low-frequency noise may create difficulty when processing the detected signal. For instance, for a heart rate monitor designed to extract a heart rate from the detected signal, low-frequency noise in the detected signal may cause the heart rate monitor's circuitry to expend additional power during the extraction, and in some cases may produce error in the extracted heart rate.

In some examples, it may be beneficial for a system to intermittently illuminate the region, rather than providing time-invariant or slowly-varying illumination. Such a system may high-pass filter the detected signal by removing or attenuating low frequencies in the detected signal. The combination of intermittent illumination and high-pass filtering of the detected signal may help reduce the effects of low-frequency noise. For instance, removing low-frequency noise from the detected signal may reduce the computation requirements on a processing circuit that extracts the heart rate from the detected signal. In addition, in some examples, it may be beneficial to replace the photodiode-derived signal with a time-invariant signal during times when the region is not illuminated. This may further reduce the computation requirements on a processing circuit that extracts the heart rate from the detected signal, and in some cases, may improve the accuracy of the extract heart rate.

In some examples, a system may intermittently illuminate a region, detect light from the intermittently illuminated region to form a detected signal, and process the detected signal with a demodulator. The demodulator may include a capacitor having an input to receive the detected signal, a resistor having an input connected to an output of the capacitor at a connection point, and a switch that connects the connection point to ground during times when the region is not illuminated. An output of the resistor may produce an output signal that is a high-pass filtered version of the detected signal during times when the region is illuminated, and a time-invariant ground signal during times when the region is not illuminated. Such a demodulator may reduce the effects of low-frequency noise sources, such as background light, op-amp offsets related to input bias, photodiode 1/f noise and dark current.

Figure 1:
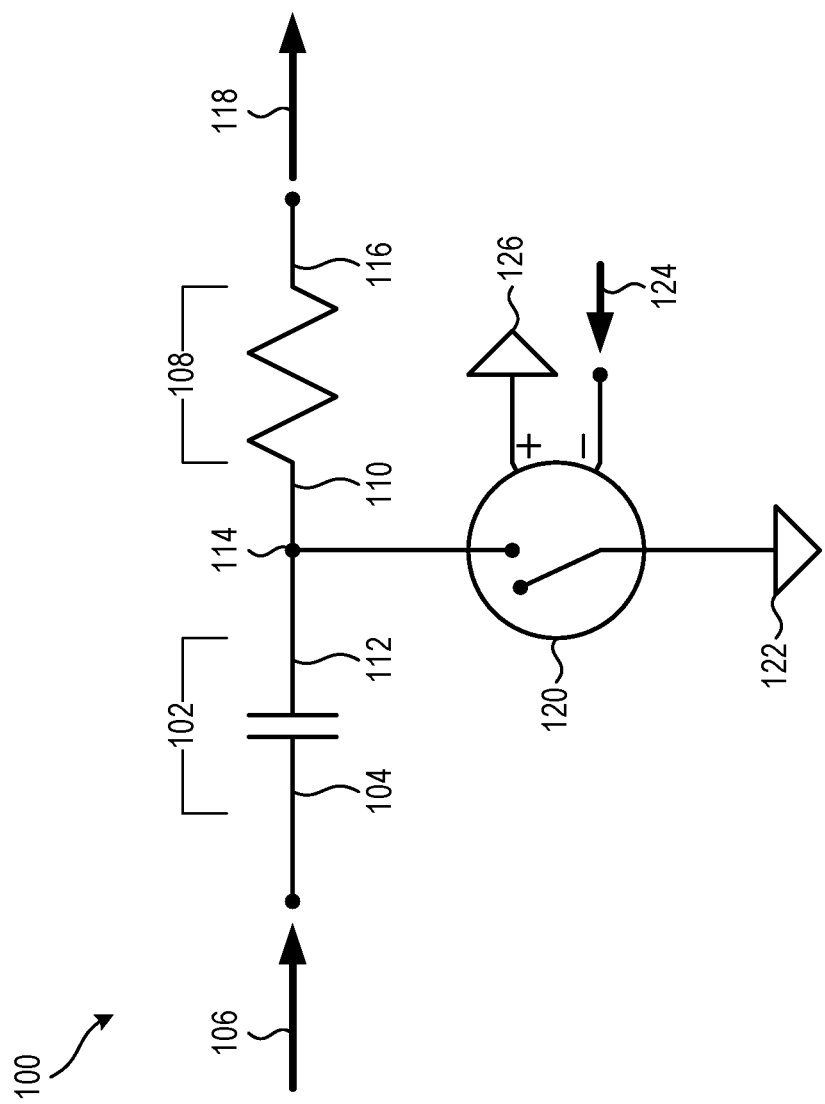
FIG. 1 is a circuit diagram showing an example of a demodulator circuit, in accordance with some embodiments.

FIG. 1 is a circuit diagram showing an example of a demodulator circuit 100, in accordance with some embodiments. The demodulator circuit 100 may be part of larger system (shown in FIG. 2 and described below). The demodulator circuit 100 of FIG. 1 is but one example; other suitable demodulator circuits may also be used.

Figure 2:
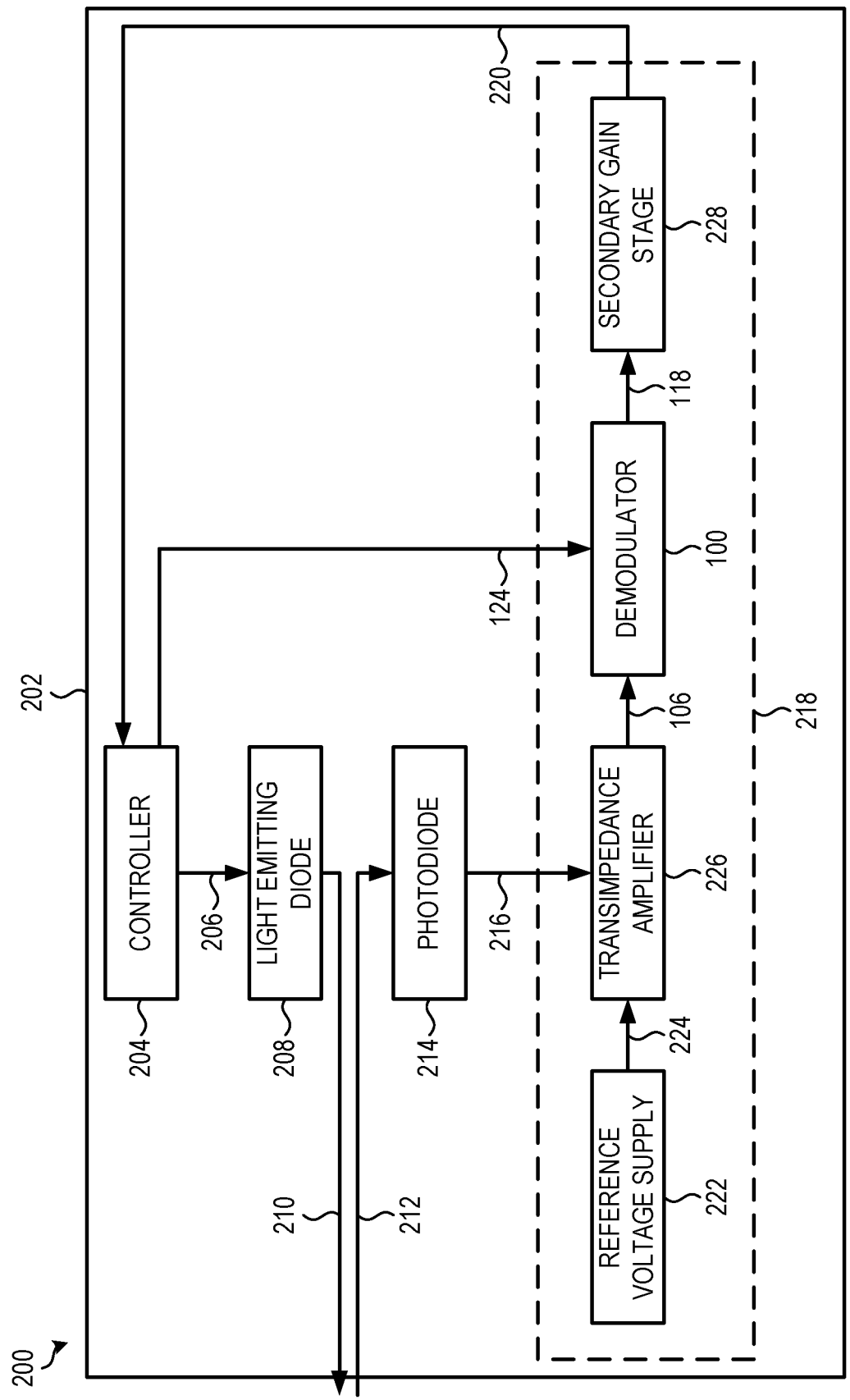
FIG. 2 is a block diagram showing an example of an illumination/detection system that includes the demodulator of FIG. 1, in accordance with some embodiments.

A capacitor 102 may have an input 104 configured to receive a time-varying input signal 106. The time-varying input signal 106 may be an amplified output of a photodiode configured to detect light from an intermittently illuminated region. FIG. 2 below shows an example of a suitable photodiode and amplifier, which may be used with the demodulator circuit 100 of FIG. 1. In some examples, the region is illuminated when an illuminating trigger voltage 124 exceeds a specified threshold voltage 126. FIG. 2 below shows an example of a suitable controller that may generate a suitable illuminating trigger voltage 124.

A resistor 108 may have an input 110 electrically connected to an output 112 of the capacitor 102 at a connection point 114. The resistor 108 may have an output 116 configured to generate a time-varying output signal 118. The resistor 108 and capacitor 102 may be connected in series between the time-varying input signal 106 and the time-varying output signal 118.

A switch 120 may connect the connection point 114 to ground 122 during times when the region is not illuminated. In some examples, the switch 120 may connect the connection point 114 to ground 122 when the illuminating trigger voltage 124 is below the specified threshold voltage 126. In other examples, the switch 120 may connect the connection point 114 to ground 122 when the illuminating trigger voltage 124 is above, rather than below, the specified threshold voltage 126.

The time-varying output signal 118 may be a high-pass filtered version of the time-varying input signal 106 during times when the region is illuminated, and a time-invariant ground signal during times when the region is not illuminated.

In some examples, the illuminating trigger voltage 124 may include a series of pulses that toggle between a relatively high voltage, such as 3 volts, and a relatively low voltage, such as 0 volts. These are but numerical examples of voltage values; other suitable voltages may also be used. In some examples, the specified threshold voltage 126 may be selected to fall between the relatively high voltage and the relatively low voltage, such as halfway between the relatively high voltage and the relatively low voltage. For instance, for the example of a relatively high voltage of 3 volts and a relatively low voltage of 0 volts, the specified threshold voltage 126 may be selected to be 1.5 volts. This is but one numerical example; other suitable numerical values can also be used.

In some examples, the illuminating trigger voltage 124 may include a series of pulses having a time-invariant pulse-to-pulse spacing and a time-invariant pulse duration. In some examples, the pulses may have a rising edge-to-rising edge spacing less than or equal to 125 milliseconds. In some examples, the pulses may have a duration less than or equal to 10 milliseconds. In some examples, the pulses may have a duration less than or equal to 1 millisecond. In some examples, these numerical values may be used to extract a heart rate of a human subject, typically in the range between 50 and 200 beats per minute. These numerical values are but examples; any other suitable numerical values may also be used.

FIG. 2 is a block diagram showing an example of an illumination/detection system 200 that includes the demodulator of FIG. 1, in accordance with some embodiments. The illumination/detection system 200 of FIG. 2 is but one example of a system that may include the demodulator of FIG. 1; other suitable systems and other suitable demodulators may also be used.

The illumination/detection system 200 may include a housing 202. In some examples, the housing 202 may be a human-wearable housing, such as a watch. The housing 202 may surround the various optical and electrical components discussed below. In some examples, the housing 202 may include a display, upon which the illumination/detection system 200 may visually display a heart rate, such as with a numerical readout. In some examples, the housing 202 may include one or more wireless transmitters and/or one or more wireless receivers, through which the illumination/detection system 200 may communicate with a wireless network and/or one or more other wireless devices. In some examples, the housing 202 may include at least one battery (not shown), and, optionally at least one wired or wireless port through which the battery may be charged.

The illumination/detection system 200 may include a controller 204. Controller 204 may include a processor, memory, and instructions stored in memory, that, when executed by the processor, cause the processor to communicate with other components in the illumination/detection system 200 (discussed below), extract a heart rate from a data signal, optionally display the extracted heart rate on a display, and optionally communicate the extracted heart rate to a network or other device.

The controller 204 may produce an illumination control signal 206, which may control a light emitting diode 208. The controller 204 may set the illumination control signal 206 to a first voltage when the light emitting diode 208 is to be turned on, and a second voltage when the light emitting diode 208 is to be turned off. In some examples, the illumination control signal 206 may be split off from the illuminating trigger voltage 124. In other examples, the controller 204 may generate illumination control signal 206 independently from the illuminating trigger voltage 124.

The light emitting diode 208 may be positioned within the housing 202 to direct light 210 out of the housing 202 to intermittently illuminate the intermittently illuminated region. In some examples, the light emitting diode 208 emits light 210 in the green portion of the electromagnetic spectrum, with a central wavelength between 495 nm and 570 nm, although other suitable wavelengths or wavelength ranges may also be used. In some examples, element 208 may include multiple light emitting diodes, optionally with at least two of the light emitting diodes emitting light 210 at different central wavelengths.

A photodiode 214 may be may be positioned within the housing 202 to detect light 212 reflected and/or scattered from the intermittently illuminated region. The photodiode 214 may produce a time-varying photocurrent 216 in response to a time-varying amount of optical power incident on the photodiode 214. The photodiode 214 may be biased with a suitable bias voltage.

A transimpedance amplifier 226 may amplify the photocurrent 216 from the photodiode 214 to produce the time-varying input signal 106 that drives the demodulator 100 (see FIG. 1). A reference voltage supply 222 may provide a constant, direct current (DC) voltage 224 to the transimpedance amplifier 226.

The demodulator 100 (see FIG. 1) may receive the illuminating trigger voltage 124 and the time-varying input signal 106, and may produce the time-varying output signal 118. The time-varying output signal 118 may include a high-pass filtered version of the time-varying input signal 106 during times when the region is illuminated, and a time-invariant ground signal during times when the region is not illuminated.

A secondary gain stage 228 may amplify the time-varying output signal 118 to produce an amplified time-varying output signal 220. The secondary gain stage 228 may direct the amplified time-varying output signal 220 to the controller 204, for downstream processing.

The reference voltage supply 222, the transimpedance amplifier 226, the demodulator 100, and the secondary gain stage 228 may be grouped together to form an amplifier 218. In some examples, such an amplifier 218 may be formed as dedicated circuitry on a chip, which may receive the photocurrent 216 and the illuminating trigger voltage 124 from elements off the chip, and may direct the amplified time-varying output signal 220 to the controller 204.

FIGS. 3-6 are circuit diagrams showing an examples of circuits that may be used with the illumination/detection system of FIG. 2, in accordance with some embodiments. The reference voltage supply 322, transimpedance amplifier 426, demodulator 500, and secondary gain stage 628 shown in FIGS. 3-6, respectively, are intended to provide non-limiting examples of circuitry for the reference voltage supply 222, transimpedance amplifier 226, demodulator 100, and secondary gain stage 228 shown in FIG. 2.

Figure 3:
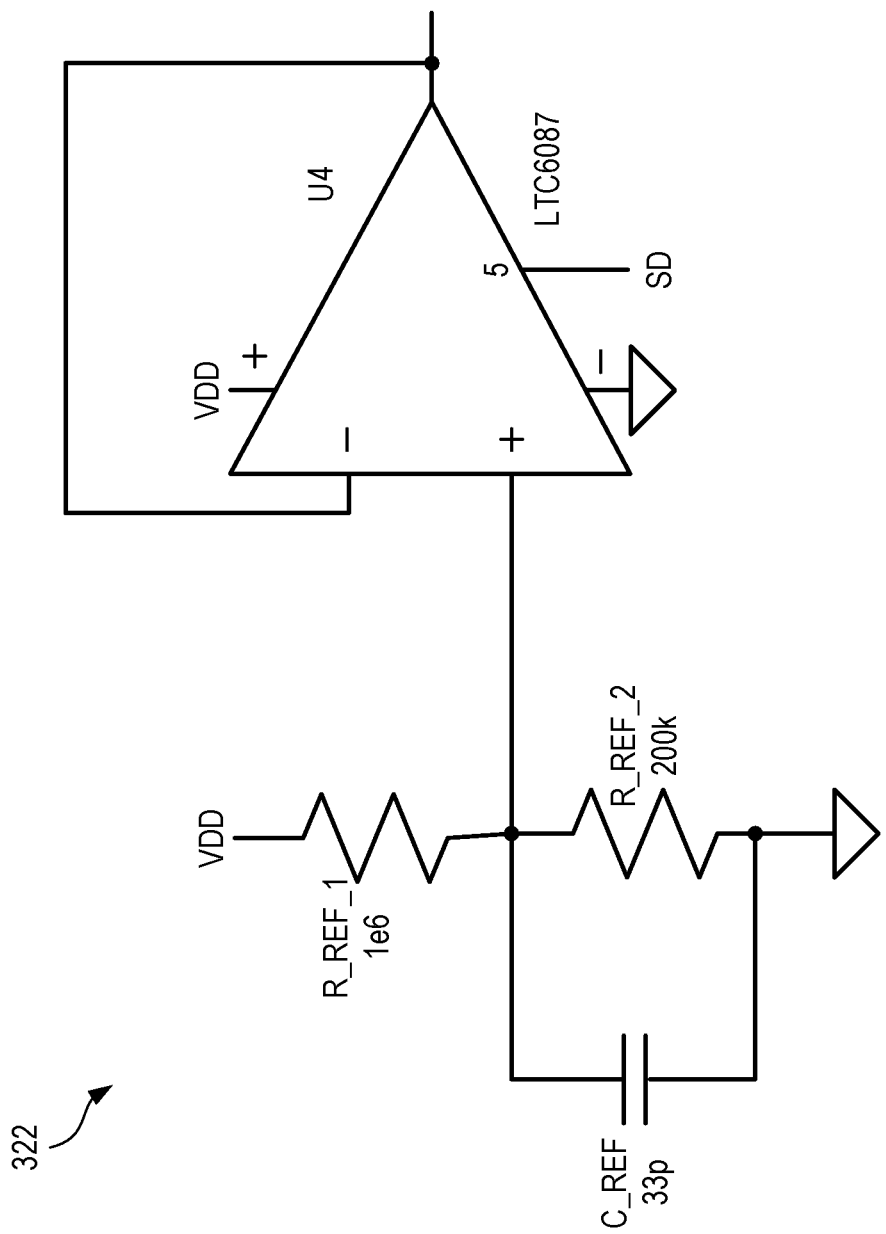
FIG. 3 is a circuit diagram showing an example of a reference voltage supply circuit that may be used with the illumination/detection system of FIG. 2, in accordance with some embodiments.

FIG. 3 is a circuit diagram showing an example of a reference voltage supply circuit 322 that may be used with the illumination/detection system of FIG. 2, in accordance with some embodiments. C_REF is a capacitor for the reference voltage supply, which may have a capacitance of 33 pF or another suitable value. R_REF_1 is a first resistor for the reference voltage supply, which may have a resistance of 1 MΩ or another suitable value. R_REF_2 is a second resistor for the reference voltage supply, which may have a resistance of 200 kΩ or another suitable value. VDD is a power line voltage, which may have a value of 3 volts or another suitable value. SD is a shutdown signal.

Figure 4:
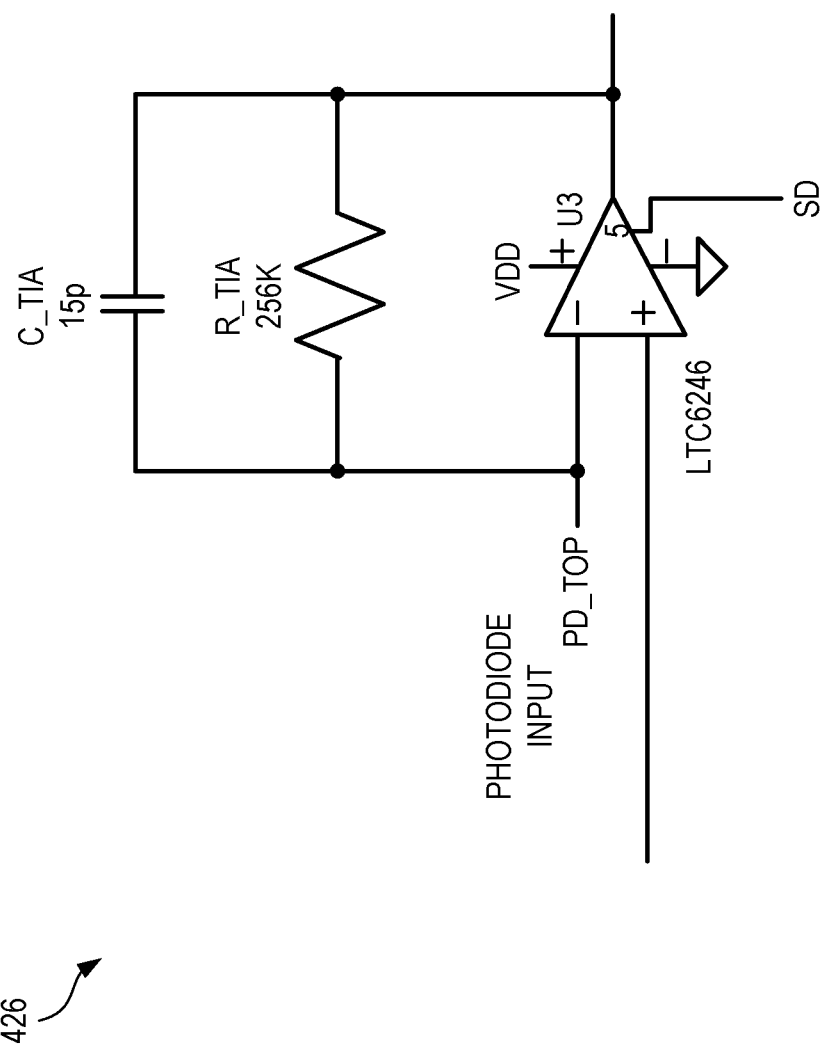
FIG. 4 is a circuit diagram showing an example of a transimpedance amplifier circuit that may be used with the illumination/detection system of FIG. 2, in accordance with some embodiments.

FIG. 4 is a circuit diagram showing an example of a transimpedance amplifier circuit 426 that may be used with the illumination/detection system of FIG. 2, in accordance with some embodiments. C_TIA is a capacitor for the transimpedance amplifier, which may have a capacitance of 15 pF or another suitable value. R_TIA is a resistor for the transimpedance amplifier, which may have a resistance of 256 kΩ or another suitable value. PD_TOP is a photocurrent produced by the photodiode (PD). VDD is a power line voltage, which may have a value of 3 volts or another suitable value. SD is a shutdown signal.

Figure 5:
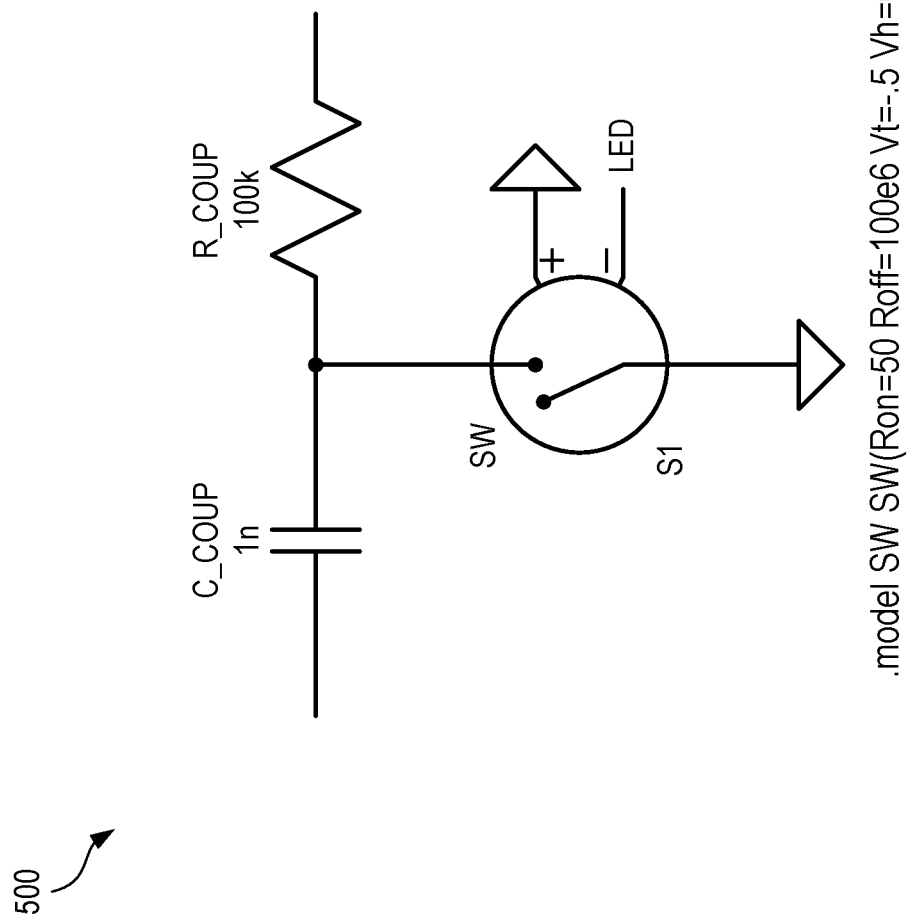
FIG. 5 is a circuit diagram showing an example of a demodulator circuit that may be used with the illumination/detection system of FIG. 2, in accordance with some embodiments.

FIG. 5 is a circuit diagram showing an example of a demodulator circuit 500 that may be used with the illumination/detection system of FIG. 2, in accordance with some embodiments. C_COUP is a capacitor for the demodulator, which may have a capacitance of 1 nF or another suitable value. R_COUP is a resistor for the demodulator, which may have a resistance of 100 kΩ or another suitable value. SW is a switch, having a resistance of 50Ω or another suitable value when the switch is closed and a resistance of 100 MΩ or another suitable value when the switch is closed. SW responds to a threshold voltage Vt of −0.5 volts or another suitable value, and has a ground voltage Vh of 0.05 volts or another suitable value.

Figure 6:
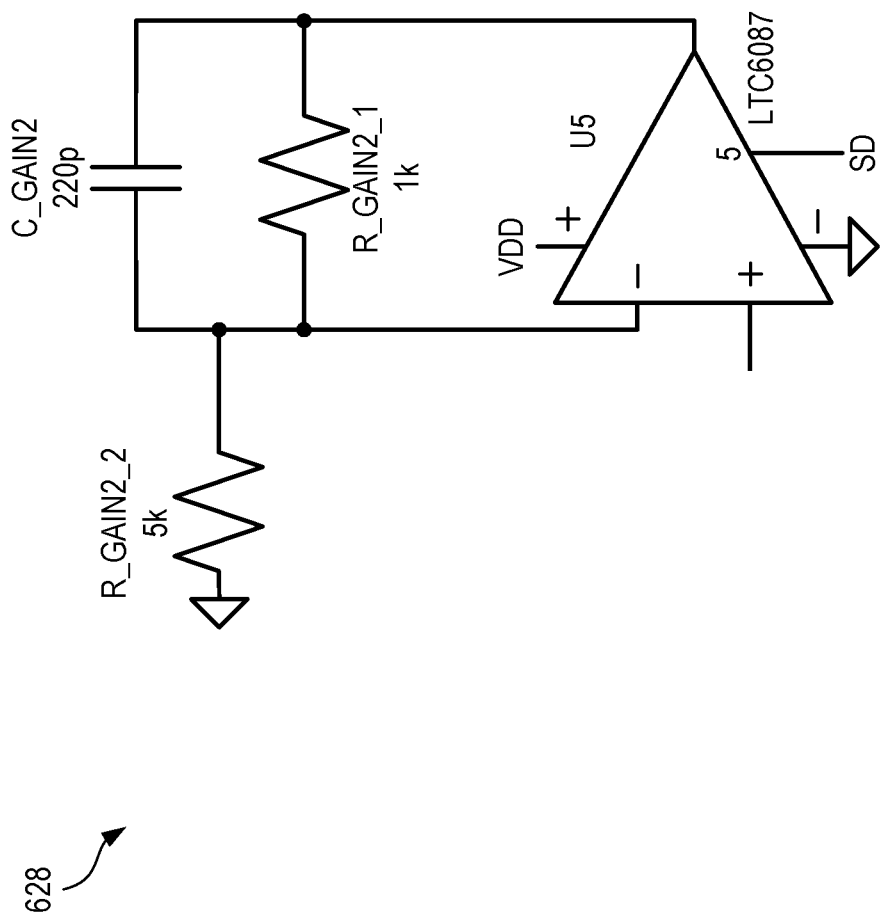
FIG. 6 is a circuit diagram showing an example of a secondary gain stage circuit that may be used with the illumination/detection system of FIG. 2, in accordance with some embodiments.

FIG. 6 is a circuit diagram showing an example of a secondary gain stage circuit 628 that may be used with the illumination/detection system of FIG. 2, in accordance with some embodiments. C_GAIN2 is a capacitor for the secondary gain stage, which may have a capacitance of 200 pF or another suitable value. R_GAIN2_1 is a first resistor for the secondary gain stage, which may have a resistance of 1 kΩ or another suitable value. R_GAIN2_2 is a second resistor for the secondary gain stage, which may have a resistance of 5 kΩ or another suitable value. VDD is a power line voltage, which may have a value of 3 volts or another suitable value. SD is a shutdown signal.

Any numerical values of resistance, capacitance, or voltage, and any part numbers, are intended to be used as non-limiting examples; other suitable values of resistance, capacitance, voltage, and/or part numbers, may also be used.

Figure 7:
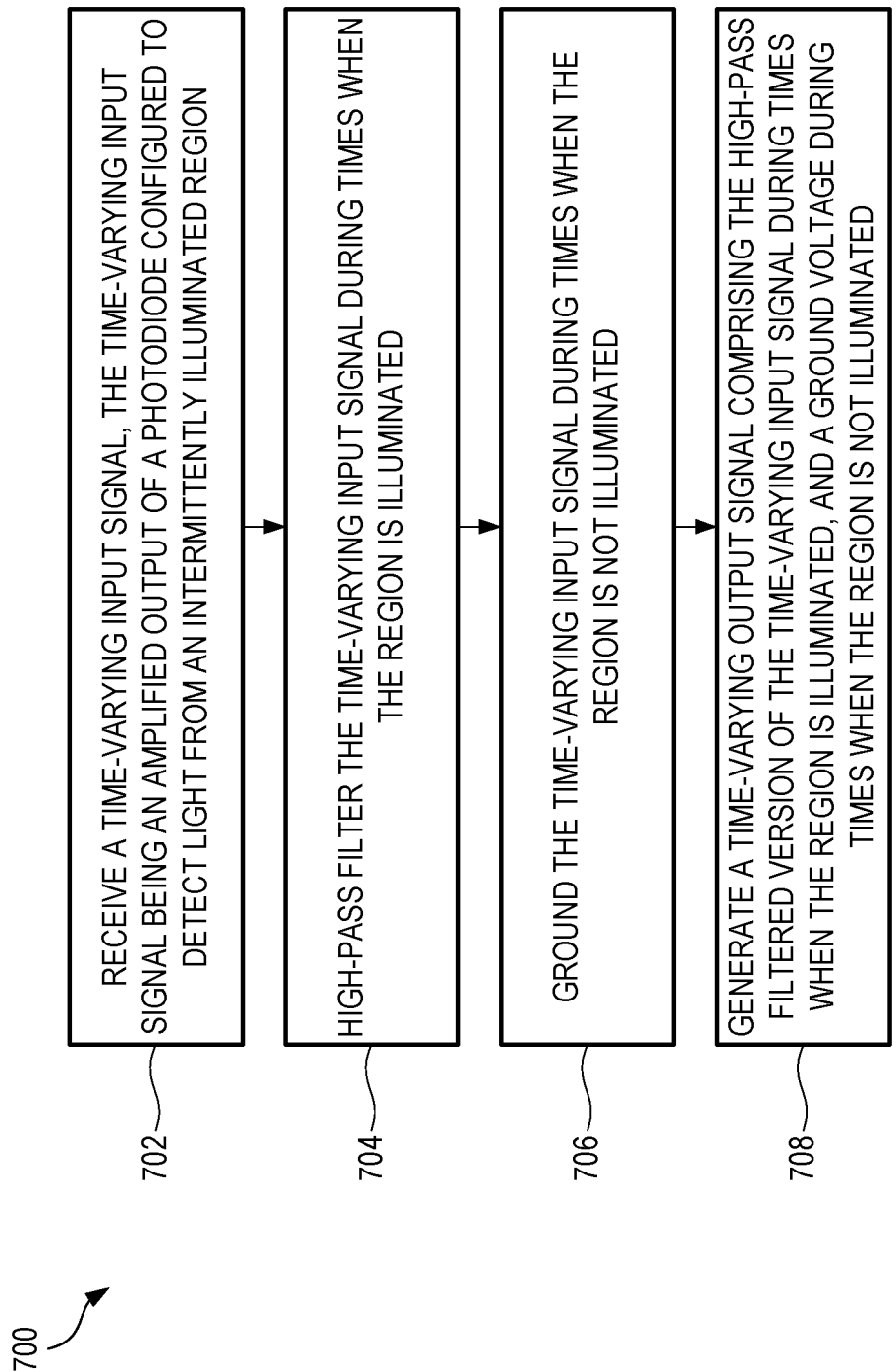
FIG. 7 is a flow chart showing an example of a method that may be used with the demodulator of FIG. 1, in accordance with some embodiments.

FIG. 7 is a flow chart showing an example of a method 700 that may be used with the demodulator of FIG. 1, in accordance with some embodiments. The method 700 may also be used with other demodulators. The method 700 is but one example of a method that may be used with the demodulator of FIG. 1; other suitable methods may also be used.

At operation 702, the demodulator may receive a time-varying input signal, such as 106 (FIG. 1). The time-varying input signal may be an amplified output of a photodiode configured to detect light from an intermittently illuminated region.

At operation 704, the demodulator may high-pass-filter (e.g., filter out low frequencies from) the time-varying input signal during times when the region is illuminated.

At operation 706, the demodulator may ground the time-varying input signal during times when the region is not illuminated.

At operation 708, the demodulator may generate a time-varying output signal comprising the high-pass filtered version of the time-varying input signal during times when the region is illuminated, and a ground voltage during times when the region is not illuminated.

The following non-limiting list of examples may further illustrate the present systems and method suitable for use in demodulating a signal from an intermittently illuminated region.

In Example 1, a system may include a capacitor having an input configured to receive a time-varying input signal, the time-varying input signal being an amplified output of a photodiode configured to detect light from an intermittently illuminated region; a resistor having an input electrically connected to an output of the capacitor at a connection point, the resistor having an output configured to generate a time-varying output signal; and a switch configured to connect the connection point to ground during times when the region is not illuminated; wherein the time-varying output signal is a high-pass filtered version of the time-varying input signal during times when the region is illuminated, and a time-invariant ground signal during times when the region is not illuminated.

In Example 2, the system of Example 1 may optionally be configured such that the region is illuminated when an illuminating trigger voltage exceeds a specified threshold voltage; and the switch is configured to connect the connection point to ground when the illuminating trigger voltage is below the specified threshold voltage.

In Example 3, the system of any one of Examples 1-2 may optionally be configured to further include a controller configured to generate the illuminating trigger voltage.

In Example 4, the system of any one of Examples 1-3 may optionally be configured such that the illuminating trigger voltage comprises a series of pulses having a time-invariant pulse-to-pulse spacing and a time-invariant pulse duration.

In Example 5, the system of any one of Examples 1-4 may optionally be configured such that the pulses have a rising edge-to-rising edge spacing less than or equal to 125 milliseconds and a duration less than or equal to 10 milliseconds.

In Example 6, the system of any one of Examples 1-5 may optionally be configured such that the pulses have a duration less than or equal to 1 millisecond.

In Example 7, the system of any one of Examples 1-6 may optionally be configured to further include a light emitting diode positioned to intermittently illuminate the intermittently illuminated region, wherein the controller is further configured to turn on the light emitting diode when the controller switches the illuminating trigger voltage from a first voltage less than the specified threshold voltage to a second voltage greater than the specified threshold voltage; and the controller is further configured to turn off the light emitting diode when the controller switches the illuminating trigger voltage from the second voltage to the first voltage.

In Example 8, the system of any one of Examples 1-7 may optionally be configured to further include the photodiode configured to detect the light from the intermittently illuminated region.

In Example 9, the system of any one of Examples 1-8 may optionally be configured to further include a transimpedance amplifier configured to amplify a photocurrent from the photodiode to produce the time-varying input signal.

In Example 10, the system of any one of Examples 1-9 may optionally be configured to further include a reference voltage supply configured to provide a constant DC voltage to the transimpedance amplifier.

In Example 11, the system of any one of Examples 1-10 may optionally be configured to further include a secondary gain stage configured to amplify the time-varying output signal to produce an amplified time-varying output signal.

In Example 12, the system of any one of Examples 1-11 may optionally be configured such that the controller is further configured to receive the amplified time-varying output signal.

In Example 13, a system may include a light emitting diode positioned to intermittently illuminate an intermittently illuminated region; a controller configured to turn on the light emitting diode by switching an illuminating trigger voltage from a first voltage less than a specified threshold voltage to a second voltage greater than the specified threshold voltage, the controller further configured to turn off the light emitting diode by switching the illuminating trigger voltage from the second voltage to the first voltage; a photodiode configured to detect light from the intermittently illuminated region; a transimpedance amplifier configured to amplify a photocurrent from the photodiode to produce a time-varying input signal; a demodulator configured to receive the illuminating trigger voltage and the time-varying input signal, and produce a time-varying output signal, wherein the time-varying output signal is a high-pass filtered version of the time-varying input signal during times when the region is illuminated, and a time-invariant ground signal during times when the region is not illuminated; and a secondary gain stage configured to amplify the time-varying output signal to produce an amplified time-varying output signal; wherein the controller is further configured to receive the amplified time-varying output signal.

In Example 14, the system of Example 13 may optionally be configured to further include a reference voltage supply configured to provide a constant DC voltage to the transimpedance amplifier.

In Example 15, the system of any one of Examples 13-14 may optionally be configured such that the demodulator comprises: a capacitor having an input configured to receive the time-varying input signal; a resistor having an input electrically connected to an output of the capacitor at a connection point, the resistor having an output configured to generate the time-varying output signal; and a switch configured to connect the connection point to ground during times when the region is not illuminated.

In Example 16, the system of any one of Examples 13-15 may optionally be configured such that the illuminating trigger voltage comprises a series of pulses having a time-invariant pulse-to-pulse spacing and a time-invariant pulse duration; and the pulses have a rising edge-to-rising edge spacing less than or equal to 125 milliseconds and a duration less than or equal to 10 milliseconds.

In Example 17, the system of any one of Examples 13-16 may optionally be configured such that the pulses have a duration less than or equal to 1 millisecond.

In Example 18, a method may include receiving a time-varying input signal, the time-varying input signal being an amplified output of a photodiode configured to detect light from an intermittently illuminated region; high-pass filtering the time-varying input signal during times when the region is illuminated; grounding the time-varying input signal during times when the region is not illuminated; and generating a time-varying output signal comprising the high-pass filtered version of the time-varying input signal during times when the region is illuminated, and a ground voltage during times when the region is not illuminated.

In Example 19, the method of Example 18 may optionally be configured such that illumination for the intermittently illuminated region comprises a series of pulses having a time-invariant pulse-to-pulse spacing and a time-invariant pulse duration.

In Example 20, the method of any one of Examples 18-19 may optionally be configured such that the pulses have a rising edge-to-rising edge spacing less than or equal to 125 milliseconds and a duration less than or equal to 10 milliseconds.

In Example 21, the method of any one of Examples 18-20 may optionally be configured such that the pulses have a duration less than or equal to 1 millisecond.

In Example 22, a system may include means for receiving a time-varying input signal, the time-varying input signal being an amplified output of a photodiode configured to detect light from an intermittently illuminated region; means for high-pass filtering the time-varying input signal during times when the region is illuminated; means for grounding the time-varying input signal during times when the region is not illuminated; and means for generating a time-varying output signal comprising the high-pass filtered version of the time-varying input signal during times when the region is illuminated, and a ground voltage during times when the region is not illuminated.

In Example 23, the system of Example 22 may optionally be configured such that illumination for the intermittently illuminated region comprises a series of pulses having a time-invariant pulse-to-pulse spacing and a time-invariant pulse duration.

In Example 24, the system of any one of Examples 22-23 may optionally be configured such that the pulses have a rising edge-to-rising edge spacing less than or equal to 125 milliseconds and a duration less than or equal to 10 milliseconds.

In Example 25, the system of any one of Examples 22-24 may optionally be configured such that the pulses have a duration less than or equal to 1 millisecond.

Each of these non-limiting examples may stand on its own, or may be combined in various permutations or combinations with one or more of the other examples.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMS), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

What is claimed is:

1. An apparatus, comprising:
   a capacitor having an input configured to receive a time-varying input signal, the time-varying input signal being an amplified output of a photodiode configured to detect light from an intermittently illuminated region;
   a resistor having an input electrically connected to an output of the capacitor at a connection point, the resistor having an output configured to generate a time-varying output signal; and
   a switch configured to connect the connection point to ground during times when the region is not illuminated;
   wherein the time-varying output signal is a high-pass filtered version of the time-varying input signal during times when the region is illuminated, and a time-invariant ground signal during times when the region is not illuminated.

2. The apparatus of claim 1, wherein:
   the region is illuminated when an illuminating trigger voltage exceeds a specified threshold voltage; and
   the switch is configured to connect the connection point to ground when the illuminating trigger voltage is below the specified threshold voltage.

3. The apparatus of claim 2, further comprising a controller configured to generate the illuminating trigger voltage.

4. The apparatus of claim 3, wherein the illuminating trigger voltage comprises a series of pulses having a time-invariant pulse-to-pulse spacing and a time-invariant pulse duration.

5. The apparatus of claim 4, wherein the pulses have a rising edge-to-rising edge spacing less than or equal to 125 milliseconds and a duration less than or equal to 10 milliseconds.

6. The apparatus of claim 5, wherein the pulses have a duration less than or equal to 1 millisecond.

7. The apparatus of claim 3, further comprising a light emitting diode positioned to intermittently illuminate the intermittently illuminated region, wherein:
   the controller is further configured to turn on the light emitting diode when the controller switches the illuminating trigger voltage from a first voltage less than the specified threshold voltage to a second voltage greater than the specified threshold voltage; and
   the controller is further configured to turn off the light emitting diode when the controller switches the illuminating trigger voltage from the second voltage to the first voltage.

8. The apparatus of claim 1, further comprising the photodiode configured to detect the light from the intermittently illuminated region.

9. The apparatus of claim 8, further comprising a transimpedance amplifier configured to amplify a photocurrent from the photodiode to produce the time-varying input signal.

10. The apparatus of claim 9, further comprising a reference voltage supply configured to provide a constant DC voltage to the transimpedance amplifier.

11. The apparatus of claim 8, further comprising a secondary gain stage configured to amplify the time-varying output signal to produce an amplified time-varying output signal.

12. The apparatus of claim 11, wherein the controller is further configured to receive the amplified time-varying output signal.

13. A system, comprising:
    a light emitting diode positioned to intermittently illuminate an intermittently illuminated region;
    a controller configured to turn on the light emitting diode by switching an illuminating trigger voltage from a first voltage less than a specified threshold voltage to a second voltage greater than the specified threshold voltage, the controller further configured to turn off the light emitting diode by switching the illuminating trigger voltage from the second voltage to the first voltage;
    a photodiode configured to detect light from the intermittently illuminated region;
    a transimpedance amplifier configured to amplify a photocurrent from the photodiode to produce a time-varying input signal;

a demodulator configured to receive the illuminating trigger voltage and the time-varying input signal, and produce a time-varying output signal, wherein the time-varying output signal is a high-pass filtered version of the time-varying input signal during times when the region is illuminated, and a time-invariant ground signal during times when the region is not illuminated; and a secondary gain stage configured to amplify the time-varying output signal to produce an amplified time-varying output signal;

wherein the controller is further configured to receive the amplified time-varying output signal.

14. The system of claim 13, further comprising a reference voltage supply configured to provide a constant DC voltage to the transimpedance amplifier.

15. The system of claim 13, wherein the demodulator comprises:
a capacitor having an input configured to receive the time-varying input signal;
a resistor having an input electrically connected to an output of the capacitor at a connection point, the resistor having an output configured to generate the time-varying output signal; and
a switch configured to connect the connection point to ground during times when the region is not illuminated.

16. The system of claim 13, wherein:
the illuminating trigger voltage comprises a series of pulses having a time-invariant pulse-to-pulse spacing and a time-invariant pulse duration; and
the pulses have a rising edge-to-rising edge spacing less than or equal to 125 milliseconds and a duration less than or equal to 10 milliseconds.

17. The system of claim 16, wherein the pulses have a duration less than or equal to 1 millisecond.

18. A method, comprising:
receiving a time-varying input signal, the time-varying input signal being an amplified output of a photodiode configured to detect light from an intermittently illuminated region;
high-pass filtering the time-varying input signal during times when the region is illuminated;
grounding the time-varying input signal during times when the region is not illuminated; and
generating a time-varying output signal comprising the high-pass filtered version of the time-varying input signal during times when the region is illuminated, and a ground voltage during times when the region is not illuminated.

19. The method of claim 18, wherein:
illumination for the intermittently illuminated region comprises a series of pulses having a time-invariant pulse-to-pulse spacing and a time-invariant pulse duration; and
the pulses have a rising edge-to-rising edge spacing less than or equal to 125 milliseconds and a duration less than or equal to 10 milliseconds.

20. The method of claim 19, wherein the pulses have a duration less than or equal to 1 millisecond.

* * * * *